United States Patent [19]
Williams et al.

[11] Patent Number: 4,749,734
[45] Date of Patent: Jun. 7, 1988

[54] RADIATION STABILIZATION OF POLYMERIC MATERIAL

[75] Inventors: Joel L. Williams, Cary; Terry S. Dunn, Raleigh, both of N.C.

[73] Assignee: Becton, Dickinson and Company, Franklin Lakes, N.J.

[21] Appl. No.: 697,417

[22] Filed: Jan. 31, 1985

Related U.S. Application Data

[63] Continuation of Ser. No. 351,398, Feb. 23, 1982, abandoned.

[51] Int. Cl.$^4$ ................................................ C08K 5/34
[52] U.S. Cl. ..................................... 524/102; 522/75
[58] Field of Search .............. 524/99, 102; 204/159.2; 522/75

[56] References Cited

U.S. PATENT DOCUMENTS 3,537,967 11/1970 Kelley et al. ............... 204/159.2
3,940,325 2/1976 Hirao ........................ 204/159.2
4,110,185 8/1978 Williams et al. ............ 204/159.2
4,274,932 6/1981 Williams et al. ............ 204/159.2

OTHER PUBLICATIONS

Chakraborty, K. B. et al.-Chemistry and Industry, (Apr. 1, 1978) pp. 237-238.
Carlsson et al.-J. Applied Polymer Science 22, 2217-2228, (1978).
Hodgeman, D.-J. Polymer Science, 19, 807-818 (1981).
European Patent Office Application Publication No. 77 36 AI published 2-6-80.
Chakraberty, K. B. et al.: "Mechanisms of Antioxidant Action: The Behavior of Hindered Piperidine U.V. Stabilizers During Processing of LDPE"-Chemistry & Industry; Apr. 1, 1978, 237-238.

Primary Examiner—Veronica P. Hoke

[57] ABSTRACT

The present invention relates generally to semi-crystalline polymers which are suitable for stabilization by irradiation sterilization. More particularly, the present invention relates to improved additives for semi-crystalline polymers, such as propylene polymer compositions, to improve the properties of the polymer when subject to irradiation.

1 Claim, 4 Drawing Sheets

Fig. 1  POLYPROPYLENE WITH 0.1% OF FORMULA I HINDERED AMINE

Fig. 2 POLYPROPYLENE WITH 4.7 % OF MOBILIZING ADDITIVE HYDROCARBON OIL

Fig. 3 POLYPROPYLENE WITH 0.1% FORMULA I HINDERED AMINE AND 4.7 % MOBILIZING ADDITIVE (HYDROCARBON OIL)

RADIATION STABILIZATION OF POLYMERIC MATERIAL

This application is a continuation of application Ser. No. 351,398, filed Feb. 23, 1982, now abandoned.

BACKGROUND OF THE INVENTION

Semi-crystalline polymeric materials, such as polypropylene, are often employed in articles where it is necessary to subject the article to irradiation sterilization. The polymeric material without additives is subject, however, to degrading, embrittlement and discoloration during or subsequent to such irradiation. Many additives have been proposed for such semi-crystalline polymeric materials to inhibit the discoloration and degrading effects of the irradiation sterilization treatment. U.S. Pat. No. 4,100,185, for example, disclosed irradiation sterilization of semi-crystalline polymers wherein the semi-crystalline polymer has incorporated therein a non-crystalline mobilizing additive which increases the free volume of the polymer to thereby prevent embrittlement of the polymer during and subsequent to the irradiation.

PRIOR ART

U.S. patent application Ser. No. 74,250, filed Sept. 10, 1979, now U.S. Pat. No. 4,274,932, is directed to a process for sterilizing a semi-crystalline polymer which includes the steps of subjecting a semi-crystalline polymer to a sterilizing amount of high energy irradiation. The semi-crystalline polymer has a specific crystalline content of from 20 to 90% and has a narrow molecular weight distribution wherein the ratio of the weight average molecular weight to the number average molecular weight is no greater than 9. The polymer, furthermore, has incorporated therein a mobilizing amount of a non-crystalline liquid mobilizing additive which increases the free volume of the polymer and retains the flexibility thereof.

U.S. Pat. No. 3,940,325 is directed to radiation sterilized shaped articles of olefin polymers. The polymers contain from 0.01 to 0.5 percent by weight based on the weight of the olefin polymer of octadecyl 3,5-di-t-butyl-4-hydroxyhydrocinnamate and/or tetrakis methane.

U.S. Pat. No. 3,537,967 is directed to a radiation sterilized article having improved color which is manufactured from a polypropylene polymer with a substantial crystalline content which has added to it up to one percent of an ester of thiodipropionic acid as a stabilizer.

European Patent Applicaton Number 79301347.5 filed July 10, 1979 is directed to polyolefin articles, especially polypropylene hypodermic syringes, which are made more resistant to the yellow discoloration and embrittlement which accompanies sterilization by gamma irradiation by the addition to the polyolefin of a heterocyclic hindered amine.

SUMMARY OF THE INVENTION

While the prior art, as outlined above, disclosed many efforts to provide an additive to stabilize semi-crystalline polymers to prevent discoloration and degrading when subjected to irradiation sterilization, the problem persists for the use of semi-crystalline polymers used in medical articles. The present invention is directed to an improvement in the irradiation stabilization of a semi-crystalline polymer by incorporating within the polymer a combination of stabilizing agents comprising a hindered amine and a mobilizing additive.

THE DRAWINGS

DETAILED DESCRIPTION OF THE INVENTION

Figure 1:
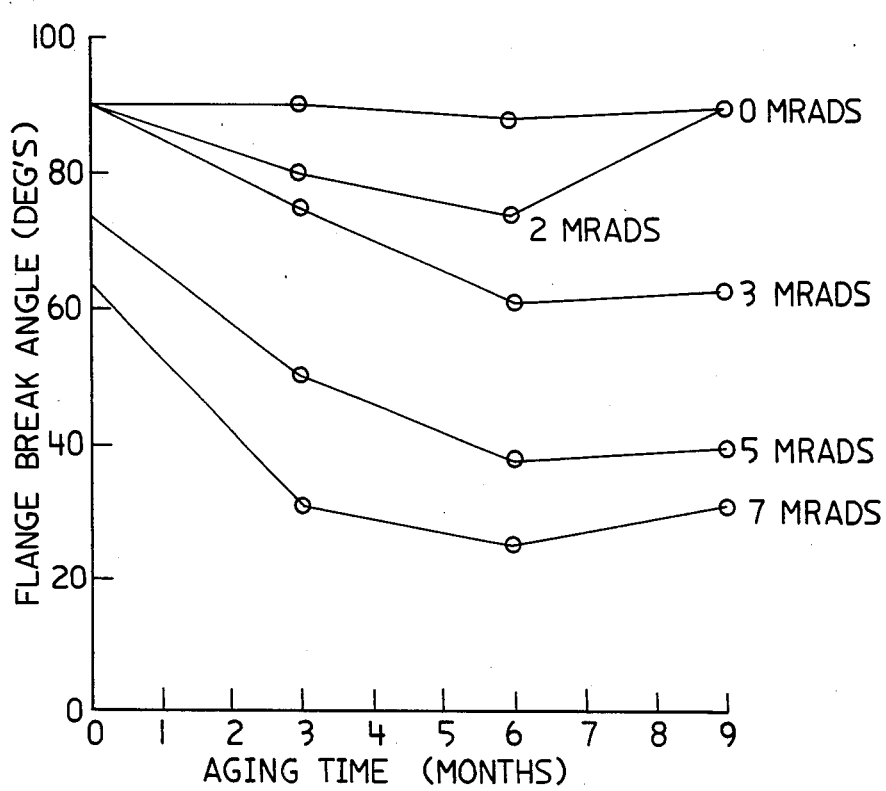
FIG. 1 is a plot of irradiation breakdown with time at various levels of irradiation for a polymer having only a hindered amine present as a stabilizer.

In accordance with one aspect of the present invention there is provided a semi-crystalline polymer which has incorporated therein a combination of stabilizing agents comprising of a heterocyclic hindered amine and a non-crystalline mobilizing additive. It has been found that the combination of a mobilizing additive and a heterocyclic hindered amine incorporated into a semi-crystalline polymer provides a synergistic improvement in the irradiation stability of such polymers. Accordingly, such semi-crystalline polymers having a combination stabilizer including a non-crystalline mobilizing additive and a heterocyclic hindered amine when subjected to sterilizing irradiation has increased stability to embrittlement and to discoloration during and subsequent to such irradiation.

The non-crystalline mobilizing additive is a low molecular weight substance which is miscible with the polymeric material and is also compatible therewith. The mobilizing additive is a substance which increases the free volume of the polymer, and therefore, also lowers the density of the polymer.

The mobilizing additive can be any one of a wide variety of liquids which increase the total free volume of the polymer. The term "liquid", as used herein, includes highly viscous substances, commonly referred to as greases. In general, such mobilizing additives have a density of from 0.6 to 1.9 g/cm$^3$ and preferably of from 0.6 to 1.1 g/cm$^3$. The mobilizing additive has a low molecular weight, with the average molecular weight being on the order of from about 100 to about 10,000 grams/mole and preferably from about 100 to about 5,000 grams/mole.

Representative examples of suitable mobilizing additives include hydrocarbon oils, halogenated hydrocarbon oils, phthalicester oils, vegetable oils, silicon oils, low molecular weight non-crystalline polymer greases, such as hydrocarbon polymer greases, low molecular weight polyester greases, polyarylether greases, etc. The preferred mobilizer is a liquid mobilizer which is not highly viscous, in particular a hydrocarbon oil or phthalicester oil.

The mobilizing additive is incorporated into the polymer in a mobilizing amount. The mobilizing additive is generally present in an amount of from about 0.01 percent to about 50 percent by weight of the polymer and preferably from 0.1 percent to about 20 percent. All percentages used herein are by weight and are based on the weight of semi-crystalline polymers unless expressly designated otherwise.

The hindered amines preferable comprise 5- to 6-membered heterocyclic ring containing the hindered amine nitrogen and optionally another hetero atom preferably nitrogen or oxygen. If the hindered amine is a tertiary amine, the tertiary group may be, for example, an alkyl, aralkyl, alkaryl or alicyclic group containing 1 to 12 carbon atoms. One or more of the substituents of the hindered amine may itself be a hindered amine so that the tertiary group may be used to link a plurality of hindered amines. The hindering groups are preferably alkyl groups containing 1 to 4 carbon atoms and most preferably all four groups are methyl. The most preferred hindered amines comprise, 2,2,4,4-tetramethyl piperidine derivatives.

The hindered amine is preferably bonded to a carrier moiety which should have little if any inhibiting effect on the chemical activity of the hindered amine. Reasonably inert carriers include aromatic compounds (for example those based on the benzene, imidazole or triazine rings), saturated hydrocarbon compounds, esters or amides of carboxylic acids, ketones and ether, thioether, sulphinyl or sulphone groups. Preferable, the carriers can be used to link together a plurality of hindered amines and hence the tertiary groups may be regarded as carriers too.

Examples of hindered amines linked by diesters or ketones include:

(a) di(2,2,6,6-tetramethyl-4-piperidyl) sebacate (see formula I) where it is the sebacate which is the carrier, (b) di-(2,2,6,6-tetramethyl-4-piperidyl) 1-(3,5-ditertiarybutyl-4-hydroxyphenylmethyl)-1,1-pentanedicarboxylate (see formula II) where it is the pentanedicarboxylate which is the carrier, (c) the condensate of succinic acid and N-(2-hydroxypropyl)-2,2,6,6-tetramethyl-4-hydroxypiperidine (see formula III) where both the succinate moiety and the tertiary propoxy groups combine to form carriers. The condensate preferably contains 6 to 20 hindered amine groups, and (d) 1,4-di-(2,2,6,6-tetramethyl-4-piperidyl)-2,3-butanedione (see formula IV) where it is the butanedione which is the carrier.

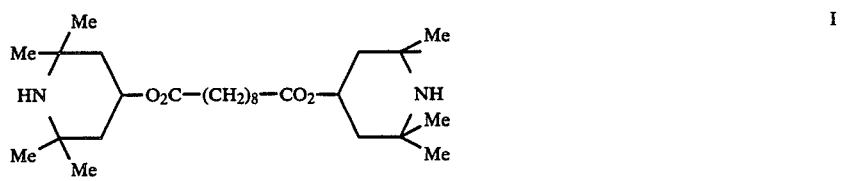

I

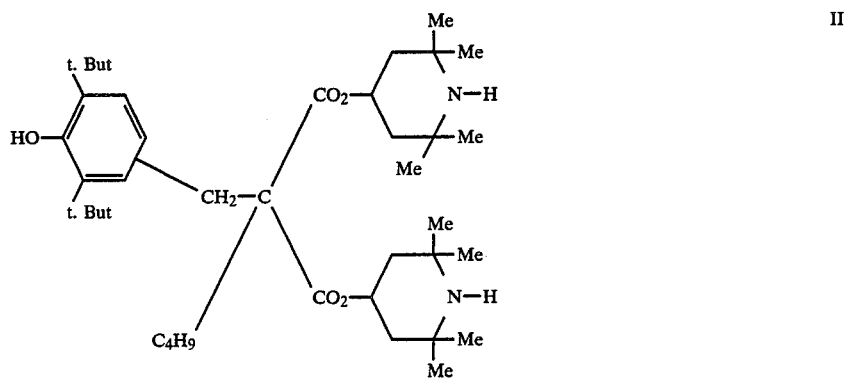

II

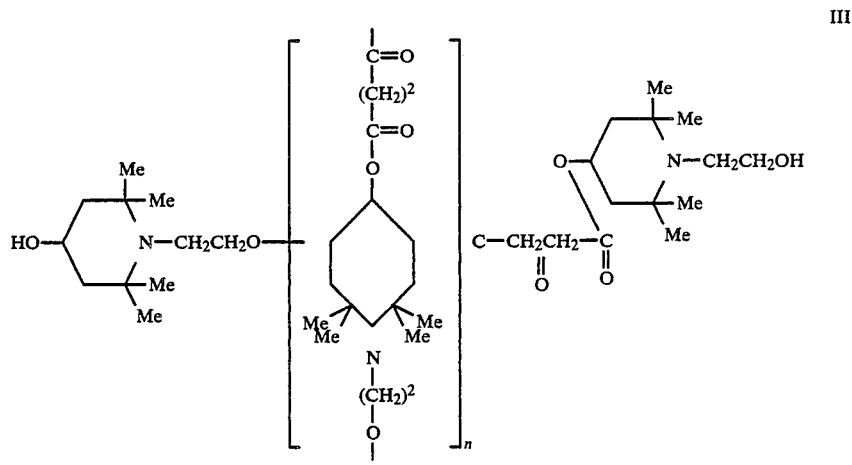

III

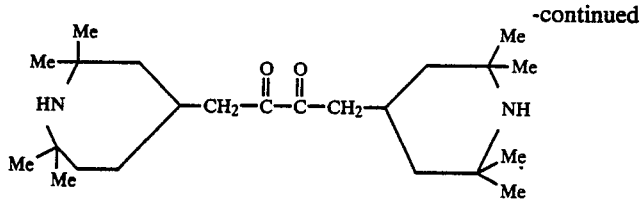

The semi-crystalline polymer can be, for example, a homopolymer of ethylene (low or high density polyethylene), propylene, butene-1 or 4-methylpentene-1 or a copolymer of two or more of these monomers. Preferred copolymers are copolymers of propylene and from 7 to 20 percent (by weight of the copolymer) of ethylene, when made by injecting ethylene into the latter stages of an otherwise homopolymerization of propylene, or from 0.5 to 10 percent of ethylene when made by random copolymerisation. Copolymers of ethylene with up to 30 percent of vinyl acetate, methyl, ethyl or butyl (including tertiary butyl) acrylates or methacrylates or acrylic or methacrylic acids may also be used. The preferred semi-crystalline polymer is polypropylene having specific crystalline content of from 20 to 90 percent.

The composition may contain stabilizing amounts (e.g., 0.01 to 2 percent by weight of the polymer) of light stabilizers (e.g. benzotriazoles) and/or phenolic antioxidants of the kind used in polyolefins, for example, n-octadecyl 3-(e,5-ditertiarybutyl-4-hydroxyphenyl)propionate. However, phenolic antioxidants may aggravate discoloration so their use may entail sacrifice of some of the improvement in discoloration. The compositions may also contain stabilizing amounts of sulphur compounds of the type known to synergise with phenolic antioxidants in polyolefins, for example, long chain (e.g. $C_{10}$ to $C_{22}$) mercaptans and sulphides but the preferred compounds are dialkyl thiodialkanoates especially when the alkyl groups contain from 10 to 22 carbon atoms and the alkanoic acids contain from 2 to 6 carbon atoms. The use of some of such sulfur compounds reduces the synergistic effect of the combination of stabilizing agents of the present invention. The compositions preferably contain from 0.01 to 10 percent (usually 0.1 to 0.5 percent) by weight of organic sulphur compound. Other conventional additives such as pigments or moulding aids may be used.

The heterocyclic hindered amine is added to the semi-crystalline polymer at a level of from about 0.005 to about 0.5 percent by weight of the polymer, preferably from about 0.05 to about 0.03 percent. It has furthermore been determined that the weight ratio of the non-crystalline mobilizing additives to the heterocyclic hindered amine should be from about 0.5 to about 20, preferably from about 2 to about 10.

While not wishing to be bound by any theory, it is believed that the mobilizing additive functions to mobilize the amorphous portion of the polymer while at the same time the presence of the hindered amine captures radicals in the accessible portions of the polymer. The net effect is believed to be that the mobilizing additive increases the radical termination reaction and prevents these reactions from affecting the bulk portion of the polymer to prevent or minimize degradation and discoloration subsequent to the irradiation. Also, the mobilizing additive aids the hindered amine in capturing radicals formed during the irradiation of the polymer.

Further features of the present invention are illustrated by the following examples.

EXAMPLE

Polypropylene containing 0.1% hindered amine (formula I) and having a melt flow of 12 and a ratio of weight to number average molecular weight $(m_w/m_n)$ of 2.8 was irradiated with 2, 3, 5, and 7 megarads of gamma radiation ($CO^{60}$). Immediately following irradiation, the sample was brittle and continued to embrittle with age as shown in FIG. 1.

Figure 2:
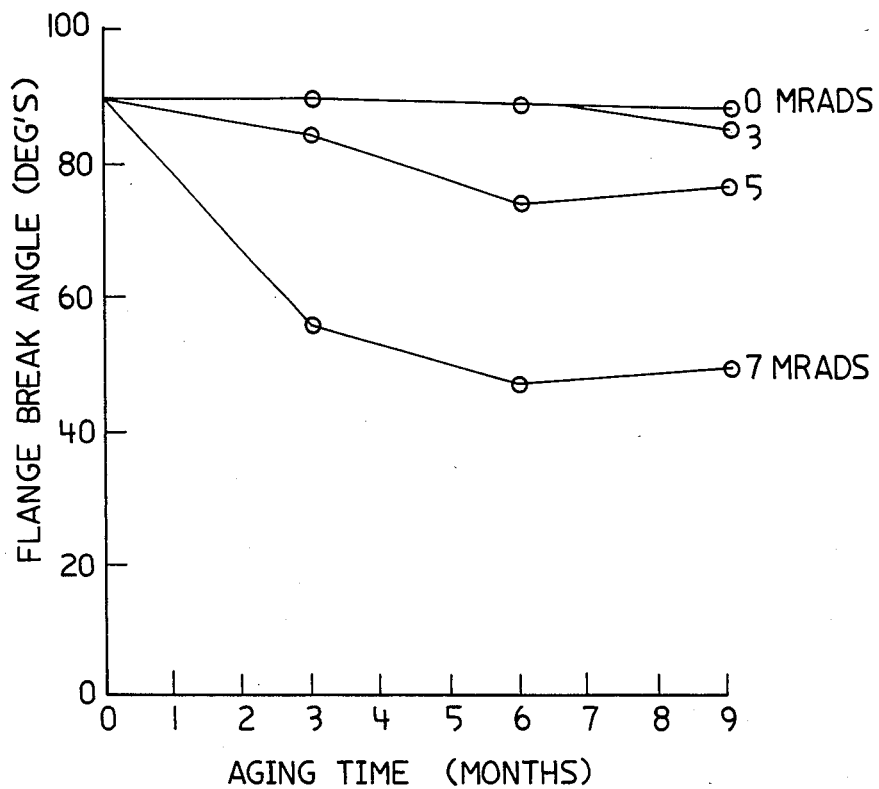
FIG. 2 is a plot of irradiation breakdown with time at various levels of irradiation for a polymer having only a mobilizing additive present as a stabilizer.

In a separate experiment, 4.7% of a mobilizing additive (hydrocarbon oil manufactured by Witco Company and identified by the trade name WITCO 300) was added to the polypropylene without the addition of hindered amine. In this case, an improvement in irradiation stability over the polypropylene with hindered amine alone was observed as shown in FIG. 2 where embrittlement was measured after 5 megarads.

Figure 3:
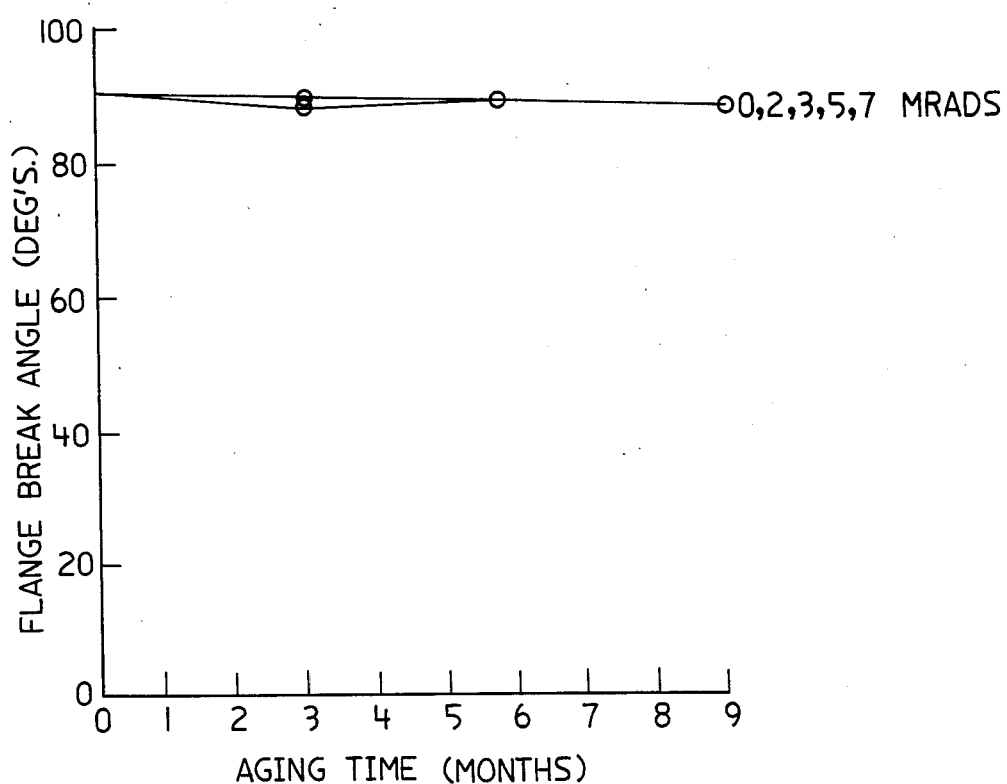
FIG. 3 is a plot of irradiation breakdown with time at various levels of irradiation for a polymer having a combination of a hindered amine and a mobilizing additive present as a stabilizer.

A dramatic improvement in irradiation stability was observed, however, when the 0.1% hindered amine (formula I) and 4.7% mobilizing additive (WITCO 300 hydrocarbon oil) were added to the polypropylene as shown in FIG. 3. In this case, the stabilized polypropylene could withstand 7 megarads without embrittlement even after 9 months of aging following irradiation. In addition, the samples contained mobilizing additive and hindered amine did not discolor with irradiation.

Thus, the combination of hindered amine with mobilizing additive produces an outstanding irradiation stabilizer package for polypropylene as disclosed herein.

Figure 4:
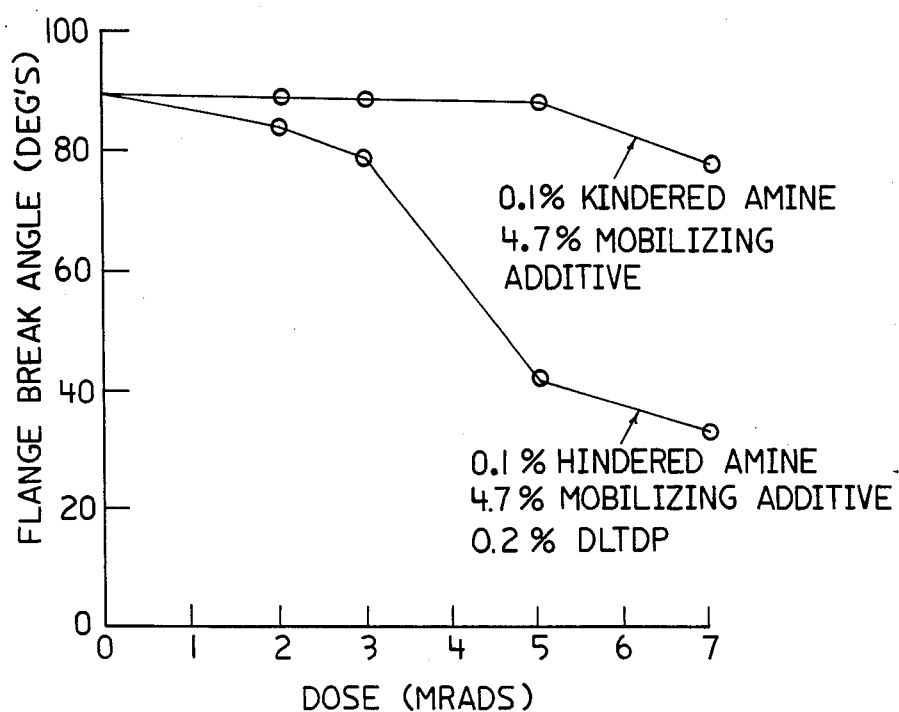
FIG. 4 is a irradiation breakdown at various levels of irradiation for a polymer containing the combination of stabilizing agents and for a polymer containing combination of stabilizing agents of the invention and also containing a commonly used sulfur compound, dilaurylthiodiproprionate (DLTDP).

The addition of thioester (dilaurylthiodipropionate) to the polypropylene containing hindered amine (0.1% formula I) and mobilizing additive (4.7% WITCO 300 hydrocarbon oil) produced a negative effect as shown in FIG. 4. It is therefore recommended that this commonly used thioester not be used in the presence of the combination of stabilizing agents of the invention due to the strong antagonistic effect which is has on polymer stability.

What is claimed is:

1. A composition having improved irradiation sterilization stability when subjected to irradiation comprising a semi-crystalline polymer having incorporated therein about 4.7 percent of hydrocarbon oil and about 0.1 percent of a hindered amine of the formula di-2,,2,6,6, tetramethyl-4-piperidyl sebacate.

* * * * *